US00PP23445P3

(12) United States Plant Patent
Lommerse

(10) Patent No.: US PP23,445 P3
(45) Date of Patent: Mar. 5, 2013

(54) *DAHLIA* PLANT NAMED 'LOMBALDEEP'

(50) Latin Name: ***Dahlia* hybrid**
Varietal Denomination: LOMBALDEEP

(75) Inventor: Henry Lommerse, Mariahout (NL)

(73) Assignee: Lommerse Holding B.V. (NL)

( * ) Notice: Subject to any disclaimer, the term of this patent is extended or adjusted under 35 U.S.C. 154(b) by 0 days.

(21) Appl. No.: 13/134,462

(22) Filed: Jun. 7, 2011

(65) Prior Publication Data

US 2012/0317691 P1 Dec. 13, 2012

(51) Int. Cl.
*A01H 5/00* (2006.01)

(52) U.S. Cl. ..... Plt./321

(58) Field of Classification Search ..... Plt./321
See application file for complete search history.

*Primary Examiner* — Kent L Bell

(74) *Attorney, Agent, or Firm* — Cassandra Bright

(57) ABSTRACT

A new and distinct *Dahlia* cultivar named 'LOMBALDEEP' is disclosed, characterized by distinctive deep red, large, ball shaped inflorescences. The new variety is a *Dahlia*, normally produced as an outdoor ornamental plant for containers or gardens.

1 Drawing Sheet

Latin name of the genus and species: *Dahlia* hybrid.
Variety denomination: 'LOMBALDEEP'.

BACKGROUND OF THE INVENTION

The new cultivar was discovered as a result of a planned breeding program directed by the inventor, Henry Lommerse a citizen of the Netherlands. The seed parent is an undistributed, unpatented proprietary variety *Dahlia* hybrid '245543' and the pollen parent is the undistributed, unpatented proprietary variety *Dahlia* hybrid '247368'. The cross resulting in 'LOMBALDEEP' was made July 2004. The new variety was discovered as a seedling in April 2005, by the inventor in a commercial research greenhouse in Mariahout, the Netherlands.

Asexual reproduction of the new cultivar 'LOMBALDEEP' by vegetative cuttings was first performed in 2007, at a research greenhouse in Mariahout, the Netherlands. Multiple generations have since been produced and have shown that the unique features of this cultivar are stable and reproduced true to type in successive generations.

SUMMARY OF THE INVENTION

The cultivar 'LOMBALDEEP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LOMBALDEEP' These characteristics in combination distinguish 'LOMBALDEEP' as a new and distinct *Dahlia* cultivar:

1. Deep red flower color
2. Large ball shaped inflorescences.

PARENT COMPARISON

Plants of the new cultivar 'LOMBALDEEP' are similar to plants of the seed parent, *Dahlia* hybrid '245543' in most horticultural characteristics, however, plants of the new cultivar 'LOMBALDEEP' produce inflorescences with a deeper red coloration, and with a different overall inflorescence shape. Additionally, the new variety has a longer flower stem length than the seed parent.

Plants of the new cultivar 'LOMBALDEEP' are similar to plants of the pollen parent, *Dahlia* hybrid '247368' in most horticultural characteristics, however, plants of the new cultivar 'LOMBALDEEP' produce larger inflorescences with a deeper red coloration, and with a different overall inflorescence shape. Additionally, the new variety has a longer inflorescence stem length and overall larger plant width than the pollen parent.

COMMERCIAL COMPARISON

'LOMBALDEEP' can be compared to the commercial variety *Dahlia hybrida* 'LOMDAHYEL' patent pending, Ser. No. 12/928,138. The two varieties are very similar in most horticultural characteristics, including growth habit, and flower shape. However, plants of 'LOMBALDEEP' produce different color inflorescences, and begin first flowering earlier than 'LOMDAHYEL'.

The new variety can also be compared to the commercial variety *Dahlia hybrida*, 'LOMDAHBRS', patent pending, Ser. No. 12/924,599. Dahlia 'LOMBALDEEP' and *Dahlia* 'LOMDAHBRS' are similar in most horticultural characteristics, including a similar inflorescence color. However, plants of 'LOMBALDEEP' produce darker red inflorescences, and begin first flowering earlier than 'LOMDAHBRS'.

BRIEF DESCRIPTION OF THE PHOTOGRAPH

The accompanying photograph in FIG. 1 illustrates in full color a typical plant of 'LOMBALDEEP' grown outdoors, in Mariahout, the Netherlands, in a commercial 15 cm container. Age of the plant photographed is approximately 70 days from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'LOMBALDEEP' plants grown inside a greenhouse, during Spring months in Mariahout, the Netherlands. Plants are approximately 3 months old. The growing temperature ranged from 17° C. to 22° C. daytime and 15° C. at night. No chemical treatments were given. Measurements and numerical values represent averages of typical plant types.
Botanical classification: *Dahlia* hybrid 'LOMBALDEEP'.

PROPAGATION

Time to initiate roots: Summer: 5 to 8 days at approximately 20° C. Winter: 20 to 22 days at approximately 17° C.
Root description: Roots very fine, heavily branched, moderately fibrous, not fleshy, colored RHS Greyed-Brown 199D.
Tuber description: Not observed.
Propagation method: Vegetative cuttings.

PLANT

Growth habit: Broad spreading-upright, with flowers on top.
Pot size of plant described: 15 cm.
Height: Approximately 34.7 cm.
Plant spread: Approximately 36.5 cm.
Growth rate: Low to moderate.
Branching characteristics:
Length of primary lateral branches: 12.9 cm (excl. peduncle).
Quantity of primary lateral branches: 3.
Characteristics of primary lateral branches:
*Diameter.*—0.6 cm.
*Color.*—RHS Yellow-Green 144A, tinged RHS N199A towards the top. Upper part of branch covered with a thin waxy layer, colored Near RHS Greyed-Green 198B.
*Texture.*—Smooth, moderately glossy, Upper part of branch covered with a thin waxy layer.
*Strength.*—Moderately strong.
Internode length: 4.6 cm.

FOLIAGE

Leaf:
*Arrangement* (*single or compound*).—Compound, lowest leaves are single.
*Leaflets.*—3. Shape: Overall shape ovate. Quantity: Approximately 8 per branch (4 pairs). Average Overall Length: 13.1 cm. Average Overall Width: 15.2 cm.
*Individual leaf blades.*—Shape of blade: Ovate to elliptic. Apex: Apiculate. Base: Short attenuate. Margin: Coarsely serrate. Texture of top surface: Smooth, dull, feeling moderately rough to the touch. Texture of bottom surface: Smooth, dull, feeling moderately rough to the touch. Pubescence: No leaf pubescence. Aspect: Leaves placed in an average angle of 85° to lateral branch. Color: Young foliage upper side: Near RHS Green 137A, base lighter; RHS Yellow-Green 145C. Young foliage under side: Near RHS Yellow-Green 148B. Mature foliage upper side: Near RHS Green N137B and N137C, both colors present. Mature foliage under side: Near RHS Greyed-Green 194B. Venation: Type: Pinnate. Venation color upper side: Near RHS Yellow-Green 147B. Venation color under side: Near RHS Yellow-Green 148A. Petiole: Length: 4.9 cm. Diameter: 0.35 cm. Color: Upper side Near RHS Greyed-Purple 187A, under side RHS Yellow-Green 144A. Texture: Smooth, moderately glossy. No stipules present.

INFLORESCENCE

Natural flowering season: Spring through Summer.
Time to flowering from rooted cutting: Nine weeks.
Inflorescence type and habit: Semi-double, slightly outward in an average angle of 30° (0°=vertical).
Rate of inflorescence opening: 14 to 21 days from bud to fully opened inflorescence. 2 days from initial flowering to full blossoming.
Inflorescence longevity on plant: Approx. 2 weeks.
Persistent or self-cleaning: Persistent.
Bud:
*Shape.*—Flattened globular.
*Length.*—1.4 cm.
*Diameter.*—1.8 cm.
*Color.*—Near Greyed-Orange RHS 175D tinged RHS Yellow-Green N144A, base darker; Green 143B.
Inflorescence size:
*Diameter.*—Average 8.9 cm.
*Depth.*—Average 6.4 cm.
*Aspect.*—Slightly outward in an average angle of 30° (0°=vertical).
Ray florets:
*Quantity.*—Approx. 60.
*Arrangement.*—Rotate, in 4 rows.
*Length.*—Approximately 4.2 cm.
*Width.*—Approximately 3.1 cm.
*Shape.*—Obovate, strongly concave, base fused.
*Apex.*—Obtuse.
*Base.*—Cuneate.
*Margin.*—Entire.
*Texture, upper and lower surfaces.*—Smooth, velvety, dull.
*Color.*—When opening, upper surface: Near RHS Red 46A, but more intense. When opening, lower surface: Near RHS Red 46B. Fully opened, upper surface: Near RHS Red 46B, but more intense. Fully opened, lower surface: Near RHS 45B.
Disc florets:
*Quantity.*—Average 50 disc florets per inflorescence.
*Arrangement.*—Rotate, in approximately 4 to 6 rows.
*Length.*—Approximately 1.0 cm.
*Width.*—Approximately 0.1 cm.
*Shape.*—Tubular.
*Apex.*—Obtuse.
*Base.*—Obtuse.
*Margin.*—Entire.
*Texture, upper and lower surfaces.*—Smooth, shiny.
*Color.*—When opening: Near RHS Green-Yellow 1B. Fully opened: Near RHS Yellow 2B. Aging: Near RHS Greyed-Orange 163C.

Phyllaries:
*Quantity.*—6.
*Length.*—1.8 cm.
*Width.*—0.9 cm.
*Shape* (*overall*).—Ovate to elliptic.
*Apex.*—Bluntly acute.
*Base.*—Cuneate.
*Margin.*—Entire.
*Color.*—RHS Green 138A, upper and lower surfaces.

Peduncles:
*Length.*—16.1 cm.
*Diameter.*—0.3 cm.
*Angle.*—About 0° to the lateral branch (=straight on top of lateral branch), secondary peduncles in an average angle of 20° (0°=vertical).
*Strength.*—Strong.
*Texture.*—Smooth, slightly glossy.
*Color.*—Near RHS Yellow-Green 152A, heavily flushed RHS Greyed-Green N199A. Covered with a thin waxy layer, colored RHS Greyed-Green 198B.
*Strength.*—Strong.

Fragrance: Very faint.

REPRODUCTIVE ORGANS

Stamens:
*Number.*—Average 50 disc florets per inflorescence. Each disc floret carries an average of 5 stamen.

Anthers:
*Shape.*—Linear.
*Length.*—Approximately 0.5 cm.
*Color.*—Near RHS Yellow-Orange 22A.
*Pollen.*—Color: Near RHS Yellow 17A. Quantity: Moderate to high.

Pistil:
*Number.*—Average: 1.
*Length.*—1.0 cm.
*Style.*—Length: 0.7 cm. Color: Near RHS Yellow-Green 151B.
*Stigma.*—Shape: Cleft (2-parted). Color: Near RHS Yellow 17A. Ovary Color: Near RHS Yellow-Green 145C.

OTHER CHARACTERISTICS

Seeds and fruits: Not observed to date.

Disease/pest resistance: Neither resistance nor susceptibility to pathogens and pests common to *Dahlia* have been observed.

Temperature tolerance: The new variety tolerates temperatures between 3 to 35° C.

What is claimed is:

1. A new and distinct cultivar of *Dahlia* plant named 'LOMBALDEEP' as herein illustrated and described.

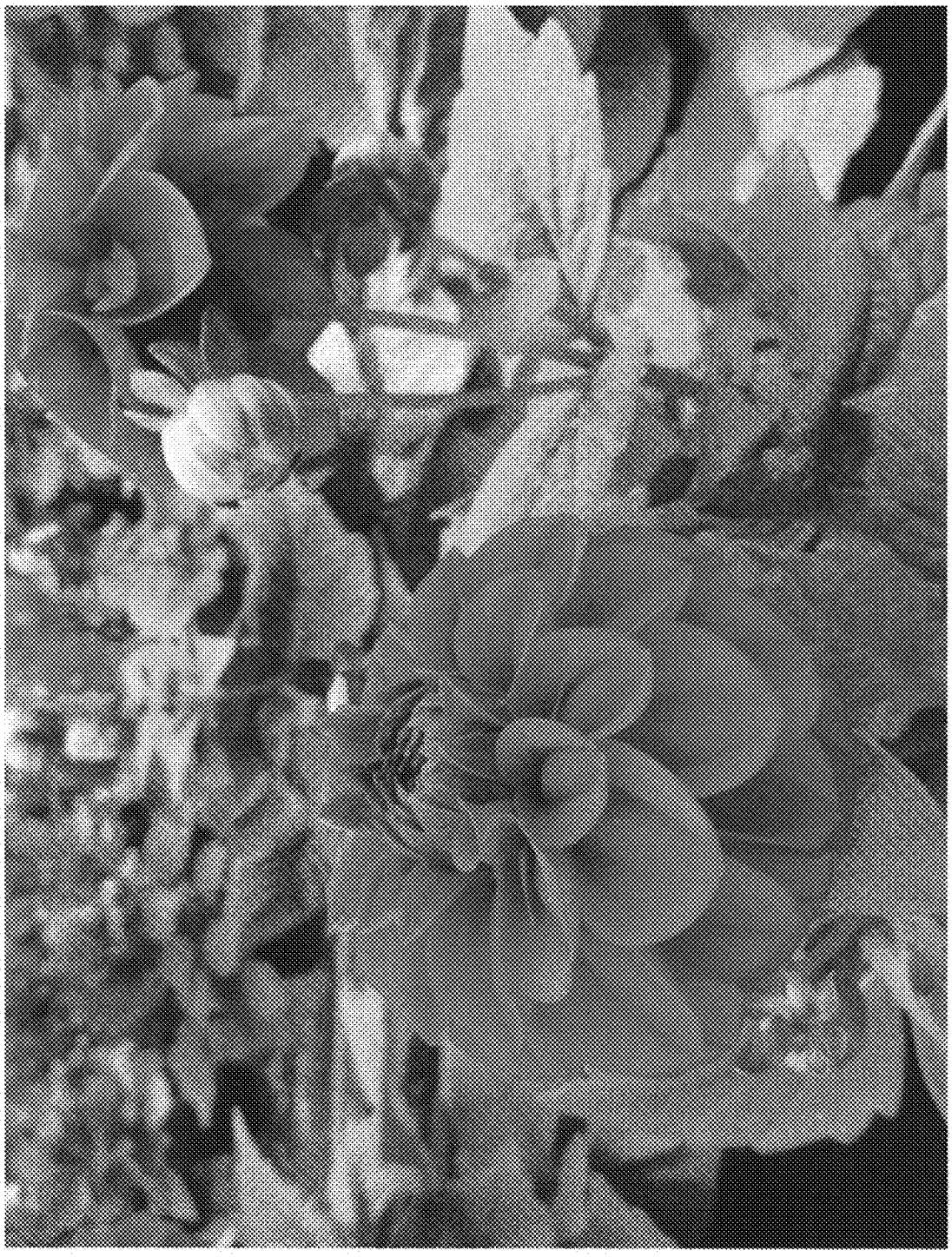

* * * * *